(12) United States Patent
Farago et al.

(10) Patent No.: US 11,819,238 B2
(45) Date of Patent: Nov. 21, 2023

(54) ROTATIONAL MEDICAL DEVICE

(71) Applicant: BOSTON SCIENTIFIC SCIMED, INC., Maple Grove, MN (US)

(72) Inventors: Laszlo Trent Farago, Hudson, WI (US); David Gordon Spangler, New Richmond, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/585,967

(22) Filed: Jan. 27, 2022

(65) Prior Publication Data

US 2022/0142667 A1    May 12, 2022

Related U.S. Application Data

(63) Continuation of application No. 16/245,065, filed on Jan. 10, 2019, now Pat. No. 11,266,436.

(60) Provisional application No. 62/615,745, filed on Jan. 10, 2018.

(51) Int. Cl.
| | |
|---|---|
| *A61B 17/22* | (2006.01) |
| *A61B 17/3207* | (2006.01) |
| *A61B 1/00* | (2006.01) |
| *A61B 17/32* | (2006.01) |
| *A61B 17/00* | (2006.01) |
| *A61B 90/00* | (2016.01) |

(52) U.S. Cl.
CPC .. *A61B 17/320758* (2013.01); *A61B 1/00133* (2013.01); *A61B 17/32002* (2013.01); *A61B 2017/00022* (2013.01); *A61B 2017/320766* (2013.01); *A61B 2090/066* (2016.02)

(58) Field of Classification Search
CPC ........ A61B 17/320758; A61B 1/00133; A61B 2017/00022; A61B 17/32002
See application file for complete search history.

(56) References Cited

U.S. PATENT DOCUMENTS

| | | | |
|---|---|---|---|
| 5,077,506 A | 12/1991 | Krause | |
| 5,372,602 A | 12/1994 | Burke | |
| 9,220,529 B2 | 12/2015 | Rivers et al. | |
| 11,529,141 B2 * | 12/2022 | Patel | ................ A61B 17/07207 |
| 11,571,210 B2 * | 2/2023 | Shelton, IV | ........... A61B 90/94 |

(Continued)

OTHER PUBLICATIONS

International Search Report and Written Opinion dated Apr. 16, 2019 for International Application No. PCT/US2019/013096.

*Primary Examiner* — Muhammad S Islam
(74) *Attorney, Agent, or Firm* — Seager, Tufte & Wickhem, LLP

(57) ABSTRACT

Medical systems and methods for making and using medical systems are disclosed. Example medical systems may include an atherectomy system configured to engage and remove plaque from walls in vessels of a vascular system. The atherectomy system may include a drive shaft, a rotational tip coupled to an end of the drive shaft, a motor coupled to the drive shaft to rotate the rotational tip, and a controller configured to control a motor state of the motor. The controller may adjust a range of possible load outputs from the motor and/or a maximum load output from the motor to account for external loads acting on the drive shaft and/or rotational tip rotated by the motor and facilitate passing an occlusion in a vasculature of a patient.

20 Claims, 9 Drawing Sheets

(56) References Cited

U.S. PATENT DOCUMENTS

| | | | |
|---|---|---|---|
| 2009/0234378 A1* | 9/2009 | Escudero | A61B 17/320758 606/159 |
| 2014/0110453 A1* | 4/2014 | Wingardner | G05B 9/02 227/175.2 |
| 2015/0201956 A1* | 7/2015 | Higgins | A61B 17/320758 606/159 |
| 2015/0272578 A1 | 10/2015 | Leimbach et al. | |
| 2016/0022307 A1* | 1/2016 | Wasdyke | A61B 17/320758 606/159 |

* cited by examiner

ROTATIONAL MEDICAL DEVICE

CROSS-REFERENCE TO RELATED APPLICATIONS

This application is a continuation of U.S. patent application Ser. No. 16/245,065, filed Jan. 10, 2019, which claims the benefit of priority under 35 U.S.C. § 119 of U.S. Provisional Application No. 62/615,745, filed Jan. 10, 2018, the entire disclosure of which is hereby incorporated by reference.

TECHNICAL FIELD

The present disclosure pertains to medical devices, and methods for manufacturing and using medical devices. More particularly, the present disclosure pertains to rotational medical devices, methods, and systems, including those with electric motors.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method, and use alternatives for medical devices and systems. In a first aspect, a medical device may comprise a drive shaft, a rotational tip coupled to a first end of the drive shaft, a motor coupled to a second end of the drive shaft and configured to rotate the rotational tip, and a controller configured to control a load output from the motor, the controller may be configured to set a maximum load output from the motor after initial rotation of the motor.

In addition or alternative and in a second aspect, the controller may be configured to determine a load output from the motor after initial rotation of the motor and set the maximum load output from the motor based on the determined load output from the motor.

In addition or alternative and in a third aspect, the controller may have a predetermined range of allowable load outputs from the motor and the controller may be configured to shift the predetermined range of allowable load outputs based on the determined load output from the motor to set the maximum load output from the motor.

In addition or alternative and in a fourth aspect, the controller may be configured to set the maximum load output from the motor to a value that is a predetermined value greater than the determined load output from the motor.

In addition or alternative and in a fifth aspect, wherein the controller may be configured to compare the determined load output from the motor to a threshold value, if the determined load output from the motor reaches or goes beyond the threshold value, set a reference load output from the motor to the threshold value, if the measured load output from the motor does not reach the threshold value, set the reference load output from the motor to the measured load output from the motor, and set the maximum load output from the motor based on the reference load output from the motor.

In addition or alternative and in a sixth aspect, the controller may be configured to set the initial load output from the motor to zero and set the maximum load output from the motor based on the reference load output from the motor.

In addition or alternative and in a seventh aspect, the controller may be configured to set the maximum load output from the motor at a predetermined level greater than zero.

In addition or alternative and in an eighth aspect, the medical device may further include a button and wherein the controller may be configured to set the reference load output from the motor to zero upon actuation of the button.

In addition or alternative and in a ninth aspect, the controller may be configured to automatically set the reference load output from the motor to zero at a predetermined time after initial rotation of the motor.

In addition or alternative and in a tenth aspect, the medical device may further include a button, and wherein the controller may be configured to set the maximum load output from the motor upon actuation of the button.

In addition or alternative and in an eleventh aspect, the controller may be configured to automatically set the maximum load output from the motor at a predetermined time after initial rotation of the motor.

In addition or alternative and in a twelfth aspect, the medical device may further include a button, and wherein the controller may be configured to set the maximum load output from the motor at a first time after initial rotation of the motor and set the maximum load output from the motor at a second time after initial rotation of the motor in response to actuation of the button, the second time is after the first time.

In addition or alternative and in a thirteenth aspect, a method of controlling a medical device may comprise determining a load output from a motor of the medical device after a startup of the motor, setting a maximum load output from the motor based on a predetermined load output amount and the determined load output from the motor, determining a control signal for the motor that is configured to establish a load output from the motor that is less than the set maximum load output from the motor, and outputting the control signal to maintain the load output from the motor below the set maximum load output from the motor.

In addition or alternative and in a fourteenth aspect, the method may further include comparing the determined load output from the motor to a threshold reference load output from the motor, if the determined load output from the motor does not reach or go beyond the threshold reference load output from the motor, setting the maximum load output from the motor to a value based on the predetermined amount of load output and the determined load output from the motor, and if the determined load output from the motor reaches or goes beyond the threshold reference load output from the motor, setting the maximum load output from the motor to a value based on the predetermined amount of load output and the threshold reference load output from the motor.

In addition or alternative and in a fifteenth aspect, the method further include setting a reference load output from the motor based on the determined load output from the motor, and wherein the set maximum load output from the motor may be based on the predetermined load output amount and the set reference load output from the motor.

In addition or alternative and in a sixteenth aspect, the reference load output from the motor may be set to zero when the determined load output from the motor has not reached or gone beyond a threshold reference load output from the motor.

In addition or alternative and in a seventeenth aspect, a controller for a medical device may comprise a processor and memory in communication with the processor, and the processor may be configured to determine a load output from a motor of the medical device, set a maximum load output from the motor based on the determined load output from the motor and store the set maximum load output in the memory, and output a control signal to the motor configured to achieve a load output from the motor that is less than the set maximum load output of the motor.

In addition or alternative and in an eighteenth aspect, the processor may be configured to compare the determined load output from the motor to a threshold reference load output from the motor, if the determined load output from the motor does not reach or go beyond the threshold reference load output from the motor, set the maximum load output from the motor to a value based on a predetermined amount of load output and the determined load output from the motor, and if the determined load output from the motor reaches or goes beyond the threshold reference load output from the motor, set the maximum load output from the motor to a value based on the predetermined amount of load output and the threshold reference load output from the motor.

In addition or alternative and in a nineteenth aspect, the controller may be configured to set the maximum load output from the motor in response to actuation of a tare button.

In addition or alternative and in a twentieth aspect, the controller may be configured to automatically set the maximum load output from the motor at a predetermined time after initial rotation of the motor.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

BRIEF DESCRIPTION

The disclosure may be more completely understood in consideration of the following description of various illustrative embodiments of the disclosure in connection with the accompanying drawings, in which.

Figure 1:
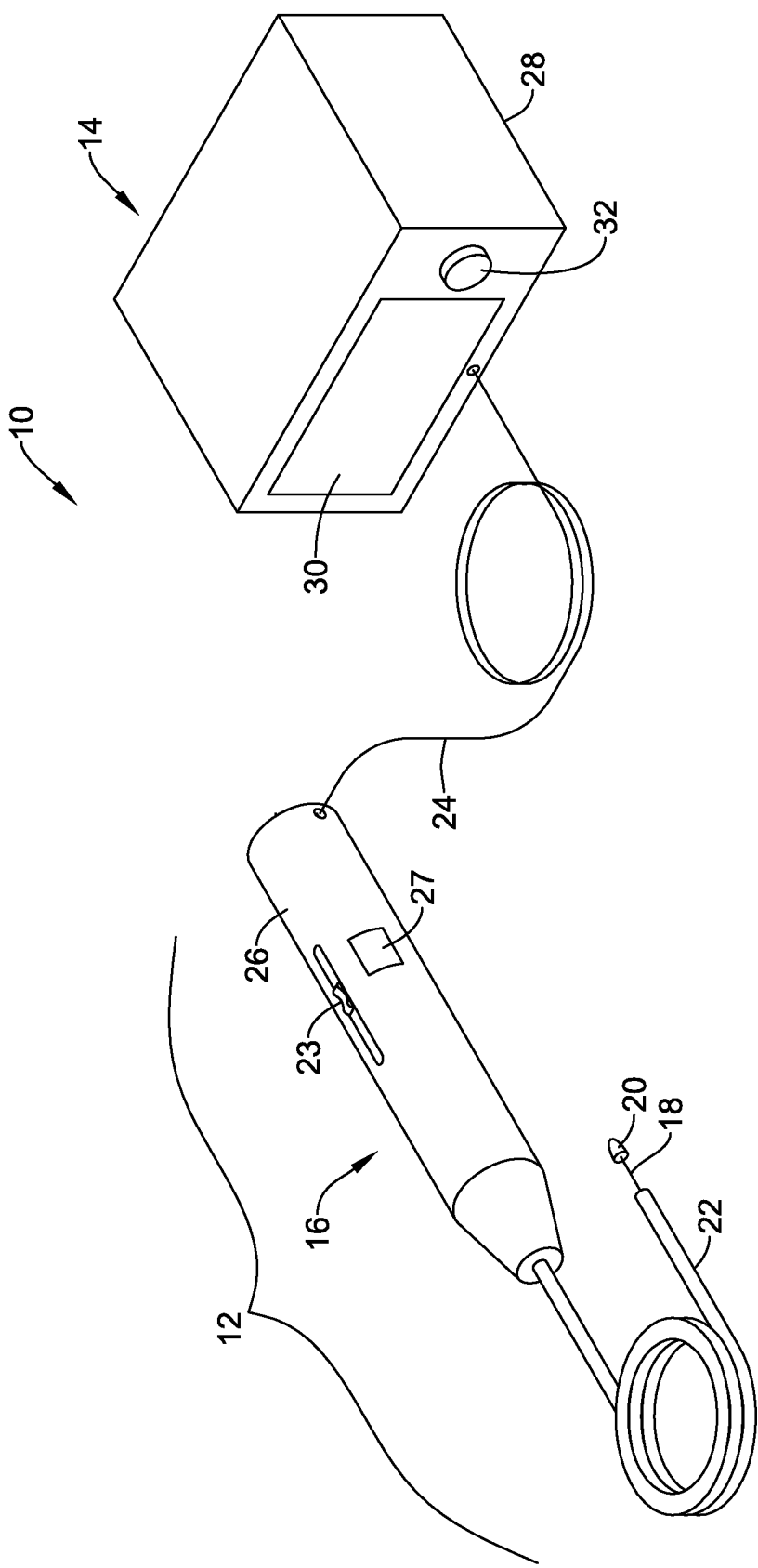
FIG. 1 is a schematic diagram of an example atherectomy system.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described herein. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", and/or other similar terms, indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits restrict blood flow and can cause ischemia in a heart of a patient, vasculature of a patient's extremities (e.g., legs, arms, head, etc.), a patient's carotid artery, and/or in other vasculature of a patient. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and a variety of catheter-based approaches which rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may be electrically driven, pneumatically driven, and/or driven in one or more other suitable manners. Additional or alternative components to those illustrated and described herein may be utilized in the operation of the atherectomy system 10.

The atherectomy system 10 may include a drive assembly 12 and a control unit 14 (e.g., a controller). Although the control unit 14 is depicted as being separate from the drive assembly 12 in FIG. 1, the functionality of the control unit 14 and the drive assembly 12 may be incorporated into a single component.

The drive assembly 12 may include, among other elements, an advancer assembly 16, a drive shaft 18 (e.g., a flexible drive shaft or other drive shaft), a rotational device 20 (e.g., a rotational tip or other rotational device), and an elongated member 22 having a first end (e.g., a proximal end), a second end (e.g., a distal end), and a lumen extending from the first end to the second end for receiving the drive shaft 18. In some cases, the elongated member 22 may be an elongated tubular member. The rotational device 20 may have a rough or sharp surface, such that it is configured to grind, abrade, cut, shave, etc. plaque from a vessel wall or other obstruction in a vessel when it is rotated.

The advancer assembly 16 may include an advancer knob 23 and may house within an advancer assembly housing 26 a motor (e.g., an electric motor, pneumatic motor, or other suitable motor) in communication with the advancer knob 23, the drive shaft 18, and the control unit 14. The advancer knob 23 may be configured to advance along a longitudinal path to longitudinally advance the motor and the rotational device 20. The motor may be coupled to the drive shaft 18 in a suitable manner including, but not limited to, a weld connection, a clamping connection, an adhesive connection, a threaded connection, and/or other suitable connection configured to withstand high rotational speeds and forces. As the drive shaft 18 may rotate over a wide range of speeds (e.g., at speeds of between zero (0) RPM and 250,000 RPM or higher), the coupling between the motor and the drive shaft 18 may be configured to withstand such rotational speeds and associated forces.

The drive shaft 18 may be formed from one or more of a variety of materials. For example, the drive shaft 18 may be formed from one or more of a variety of materials, including steel, stainless steel, and/or other suitable materials.

The drive shaft 18 may have a suitable diameter and/or length for traversing vasculature of a patient. In some cases, the drive shaft 18 may have a diameter in a range from about 0.030 centimeters (cm) or smaller to about 0.150 cm or larger and a working length in a range from about ten (10) cm or shorter to about three hundred (300) cm or longer. In one example, the drive shaft 18 may have a diameter of about 0.05715 cm and a length of about fifty (50) cm. Alternatively, the drive shaft 18 may have a different suitable diameter and/or different suitable length.

The rotational device 20 may have an outer perimeter which is equal to or larger than a distal diameter of the drive shaft 18 and/or the elongated member 22. Alternatively or in addition, the rotational device 20 may have an outer perimeter which is smaller than a diameter of the drive shaft 18 and/or the elongated member 22. The rotational device 20 may have a symmetric design so that it penetrates equally well in both rotational directions, but this is not required and the rotational device 20 may be configured to penetrate in only one direction. The diameter of the drive shaft 18 may depend on the dimension of the lumen of the elongated member 22 and/or one or more other factors.

The rotational device 20 may be coupled to the drive shaft 18. Where the drive shaft 18 has a first end portion (e.g., a proximal end portion) and a second end portion (e.g., a distal end portion), the rotational device 20 may be coupled to the drive shaft 18 at or near the second end portion. In some cases, the rotational device 20 may be located at or adjacent a terminal end of the second end portion of the drive shaft 18.

The rotational device 20 may be coupled to the drive shaft 18 in any manner. For example, the rotational device 20 may be coupled to the drive shaft 18 with an adhesive connection, a threaded connection, a weld connection, a clamping connection, and/or other suitable connection configured to withstand high rotational speeds and forces. Similar to as discussed above with respect to the connection between the drive shaft 18 and the motor, as the drive shaft 18 and/or the rotational device 20 may rotate at speeds between zero (0) RPM and 250,000 RPM or higher, the coupling between the drive shaft 18 and the rotational device 20 may be configured to withstand such rotational speeds and associated forces.

The drive assembly 12 and the control unit 14 may be in communication and may be located in or may have a same housing and/or located in or have separate housings (e.g., the advancer assembly housing 26 and a control unit housing 28 or other housings). Whether in the same housing or in separate housings, the drive assembly 12 and the control unit 14 may be communication through a wired (e.g., via one or more wires in the electrical connector 24) and/or wireless connection. Wireless connections may be made via one or more communication protocols including, but not limited to, cellular communication, ZigBee, Bluetooth, WiFi, IrDA, dedicated short range communication (DSRC), EnOcean, and/or any other suitable common or proprietary wireless protocol, as desired.

In some cases, the drive assembly 12 may include one or more control buttons configured to effect and control operations for the motor of the drive assembly 12. In one example, the drive assembly may include a button 27 configured to initiate setting or establishing a maximum load output from the motor. As shown in FIG. 1, the button 27 may be on the housing 26 of the advancer assembly 16, however, the button 27 may be located in one or more other locations in communication with electronic components configured to control operation of the motor, as desired. The button 27 may be a physical button and/or a virtual button that may be selected through a touch sensitive surface. The drive assembly 12 may include one or more button or other selectable components in addition to or as an alternative to the button 27.

Although not necessarily shown in FIG. 1, the drive assembly 12 may include and/or enclose one or more operational features. For example, among other features, the drive assembly 12 may include a motor, a control button, a control knob configured to advance the rotational device 20, rubber feet, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a motor speed (e.g., RPM or other speed) adjustment knob or other control knob). Additionally or alternatively, the control unit 14 may include one or more other features for controlling the motor and/or other features of the drive assembly 12 (e.g. one or more motor states of the motor) including, but not limited to, a processor, memory, input/output devices, a speaker, volume control buttons, on/off power supply switch, motor activation switch, a timer, a clock, and/or one or more other features.

In some cases, the control unit 14 may include one or more motor load output control mechanisms for controlling an operation of the atherectomy system 10. In one example of a motor load output control mechanism that may be included in the control unit 14, the control unit 14 may include a mechanism configured to set and/or adjust a maximum load output from the motor based on a load output of the motor that is determined after initial startup (e.g., initial rotation) of the motor. Additionally or alternatively, the control unit 14 may include other control and/or safety mechanism for controlling the operation of the atherectomy system 10 and mitigating risks to patients.

Figure 2:
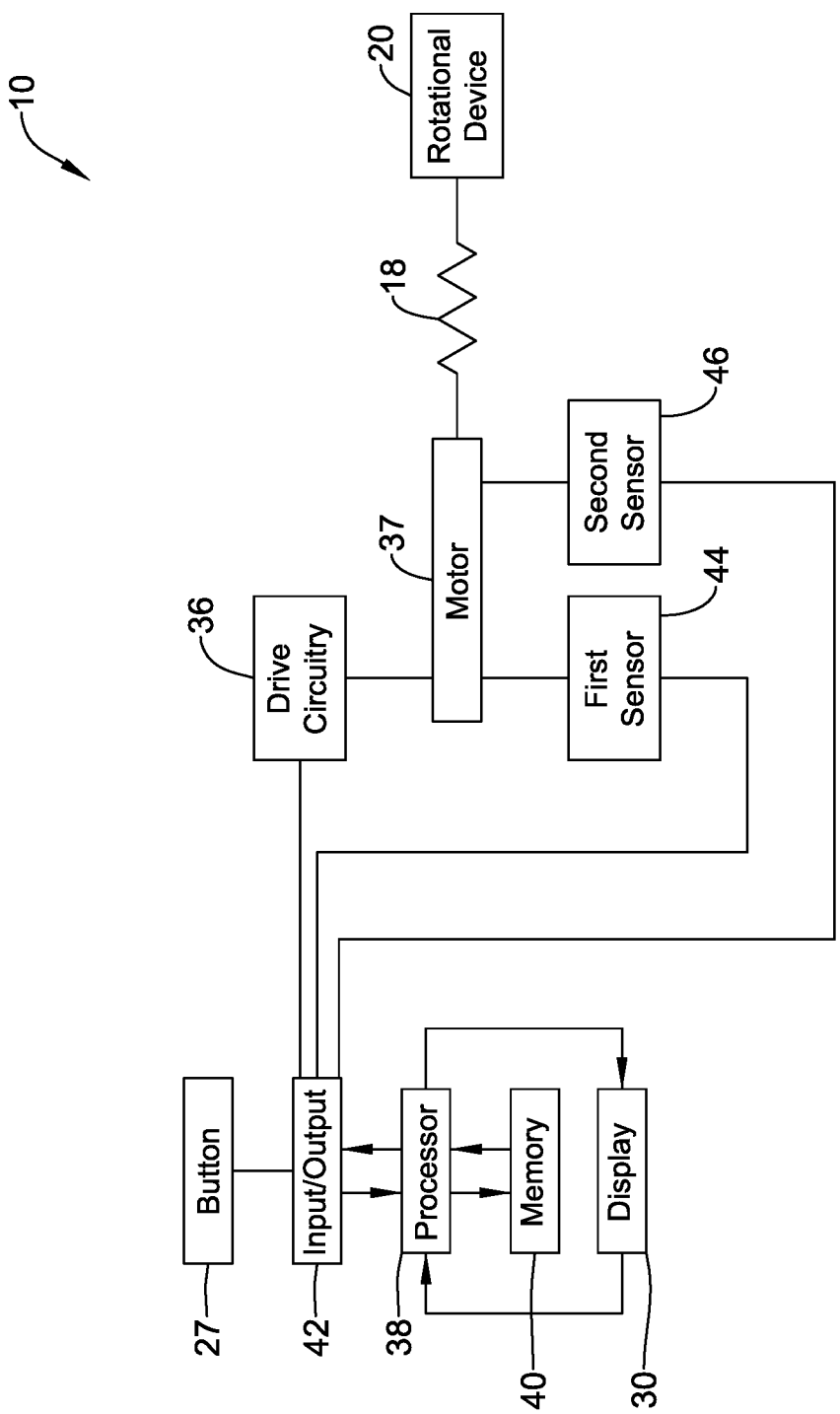
FIG. 2 is a schematic box diagram of an example atherectomy system.
Figure 3:
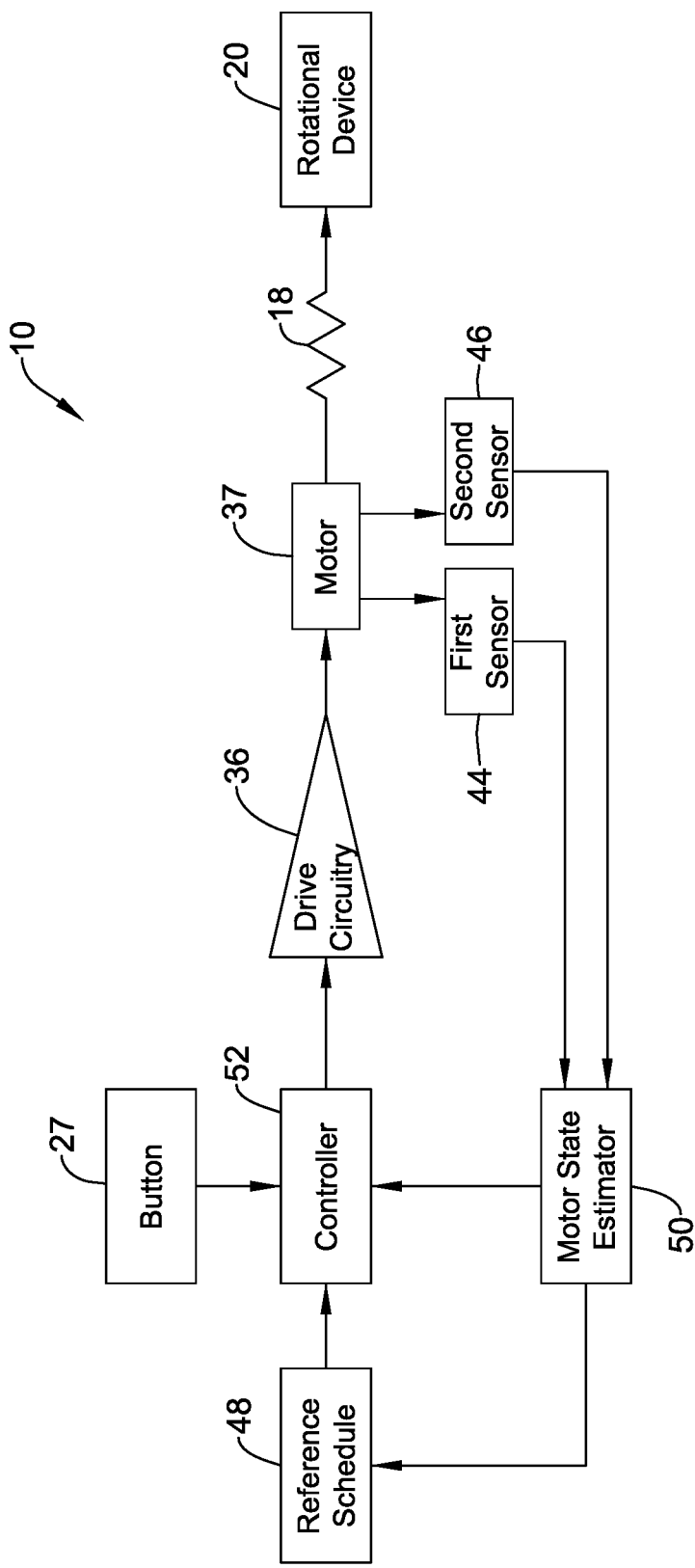
FIG. 3 is a schematic flow diagram of an example atherectomy system.

FIG. 2 depicts a block diagram of the atherectomy system 10. The atherectomy system 10 may include drive circuitry 36 (optionally included), a motor 37 (e.g., an electric motor, turbine, or other suitable drive mechanism) in communication with the drive circuitry 36, sensors (e.g., a first sensor 44, a second sensor 46, and or other suitable sensors) for sensing motor parameters (e.g., drive current, drive voltage, motor position, etc.), and the rotational device 20 in communication with the motor 37 through the drive shaft 18. Because torque may build up in the drive shaft 18, the drive shaft 18 is depicted in FIGS. 2 and 3 as a spring.

When the drive circuitry 36 is included in the atherectomy system 10, the drive circuitry 36 may be mounted on a substrate or other component in the advancer assembly housing 26 of the drive assembly 12 and may be in electrical communication with the control unit 14. The drive circuitry 36 may include, but is not required to include, a microprocessor and/or a microcontroller, an application specific integrated circuit ("ASIC"), and/or an application specific standard product ("ASSP"). In some cases, the drive circuitry 36 may be (at least partially) incorporated into the control unit 14, but this is not required.

As discussed above, the atherectomy system 10 may include one or more features configured to facilitate controlling operation of the drive assembly 12. As shown in FIG. 2, the atherectomy system 10 may include (e.g., in the control unit 14 or drive assembly 12), among other features, the button 27, a processor 38 (e.g., a microprocessor, a microcontroller, etc.), memory 40, the display 30, an input/output port 42, and/or one or more other suitable components for controlling operation of the drive assembly 12.

The processor 38 may be operatively coupled to memory 40. The memory 40 may be used to store any desired information, such as control algorithms, set points, schedules, control schedules, times, diagnostic limits, such as, for example, speed limits, RPM limits, torque limits, current limits, voltage limits, and the like. The processor 38 may be configured to access the information stored in the memory 40 to facilitate operation of the atherectomy system 10. The memory 40 may include any of one or more suitable types of storage devices including, but not limited to, RAM, ROM, EPROM, flash memory, a hard drive, and/or the like. In some cases, the processor 38 may store information within the memory 40, and may subsequently retrieve the stored information from the memory 40 to effect operation of the atherectomy device and/or for analysis. Further, the processor 38 and/or the memory 40 may include and/or be in communication with a timer (not shown).

The input/output port 42 may be configured to receive input from one or more components of the atherectomy system 10. In one example, the input/output port 42 may receive inputs from and/or provide outputs to the button 27, the drive circuitry 36, the first sensor 44, the second sensor 46, and/or one or more other components of the atherectomy system 10.

FIG. 3 depicts a schematic block diagram of control software and circuitry of the atherectomy system 10 coupled with the motor 37, which in turn is operatively attached to the drive shaft 18 and the rotational device 20. The control software and circuitry may include, among other features, the drive circuitry 36 (when included), a control schedule component 48, a motor state estimator 50 (e.g., a motor state observer or other motor state estimator), and a controller 52 (e.g., a feedback controller, a closed loop controller and/or feedback regulator, such as a proportional-integral-derivative (PID) controller or other controller). Although the control schedule component 48, the motor state estimator 50, and the controller 52 are depicted as being separate components in FIG. 3, one or more of the control schedule component 48, the motor state estimator 50, and the controller 52 may be implemented in a single controller or processor or, alternatively, multiple controllers or processors that may be configured to perform the functions of the disclosed control schedule component 48, motor state estimator 50, and the controller 52. Although not necessarily required, one or more of the control schedule component 48, the motor state estimator 50, the controller 52, the drive circuitry 36, and/or other electronic processing components of the atherectomy system 10 may be implemented on the processor 38, the memory 40, and/or the input/output port 42 (e.g., the processor 38, the memory 40, and/or the input/output port 42 may be configured to effect operation of one or more of the control schedule component 48, the motor state estimator 50, the controller 52, the drive circuitry 36, and/or other electronic processing components of the atherectomy system 10).

The control schedule component 48 may include a control schedule that relates a motor state to a motor input or set point (e.g., a reference value) for a motor state. That is, for any possible value of a motor state, the control schedule may have a related reference value (e.g., a motor input or set point for a motor state). Example motor states may include, but are not limited to, motor speed, motor position, motor torque, motor drive current, motor drive voltage, motor drive electric power, and/or other motor states. An example control schedule may relate speed to torque, speed to electric current, speed to electric voltage, and/or may relate one or more other motor states to a reference motor state. For example, a control system utilizing the control schedule that relates speed to torque may receive a speed input (e.g., from the motor state estimator 50 or other component of the atherectomy system 10) and provide a reference torque (e.g., for use the by the controller 52 or other component of the atherectomy system 10) on which a control signal may be based. Although the control schedule component 48 may be utilized for determining a control signal, it is contemplated that the controller 52 may determine a control signal without the use of a control schedule component 48 utilizing one or more known control techniques based on feedback from the motor state estimator 50 and/or other feedback information.

In some cases, the control schedule of the control schedule component 48 may be saved in memory 40 and/or other memory and accessed or otherwise utilized by the processor 38 to determine a reference value based on an input (e.g., an input motor state, such as speed). The control schedule component 48 may be or may include the memory 40, but this is not required.

The control schedule may be predetermined before operation of the atherectomy device (e.g., during calibration or pre-set by a manufacturer) and saved in the memory 40 or other memory. In some cases, a user may be able to adjust or otherwise modify the control schedule and save it in the memory 40 or other memory to establish a predetermined or off-line control schedule. The control schedule may be considered predetermined or off-line if it is not modified in real-time during operation of the drive assembly 12.

In some cases, the control schedule component 48 may include a predetermined range of load outputs from the motor 37 for passing an occlusion in a vessel of a patient. The predetermined range of load outputs may include a maximum load output from the motor 37 based on one or more factors. For example, the maximum load output may be based on a level of expected load transfer to the rotational device 20 when no external loads are acting on the drive shaft 18, the rotational device 20, and/or the elongated member 22. External loads may arise from the rotational device 20 engaging an occlusion in the patient's vessel, bending in the elongated member 22, bending in the drive shaft 18, and/or other loads that may act on the drive shaft 18, the rotational device 20, and/or the elongated member 22 during a procedure (e.g., an atherectomy procedure or other suitable procedure) As discussed in greater detail below, the controller 52 may be configured to adjust (e.g., shift or otherwise adjust in one or more other suitable manners) at least a portion of the predetermined range of load output from the motor in response to one or more external loads acting on the drive shaft 18, the rotational device 20, and/or the elongated member 22. In some cases, the controller 52 may store an adjusted predetermined range of load output from the motor 37 in the memory 40.

The motor state estimator 50 may be configured to estimate one or more states of the motor 37 based on inputs received from sensors sensing motor parameters (e.g., where sensed motor parameters may be measured motor states). Example motor parameters may include drive current, drive voltage, input power, motor position, etc. In one case, the first sensor 44 may sense an input current to the motor 37 and provide signals indicative of a value of motor drive current or other electrical input to the motor state estimator 50. Additionally, or alternatively, the second sensor 46 may sense a position of the motor 37 and provide signals indicative of a position value of the motor 37 to the motor state estimator 50. In some cases, a sensor configured to sense a position of a motor may be a Hall-effect sensor, but other position sensors may additionally or alternatively be utilized. Although sensors 44, 46 are disclosed as sensing current and motor position, these sensors may be configured to sense additional or alternative other parameters and/or other sensors may be included in the atherectomy system 10 that sense similar or different motor parameters.

Based on sensed values of motor parameters provided to the motor state estimator 50, the motor state estimator 50 may calculate (e.g., estimate) one or more motor states. In one example, based on received values indicative of motor position, timing of position values, and known relationships of motor position and time, the motor state estimator 50 may calculate or determine (e.g., estimate) a speed (e.g., RPMs or other speed parameter) of the motor 37. In another example, based on received values indicative of motor position, received values indicative of drive current or other electrical input, and known relationships of motor position to electrical input to a motor, the motor state estimator 50 may calculate or determine (e.g., estimate) a torque (e.g., a load output) of the motor 37. Additionally or alternatively, other motor states may be determined by the motor state estimator 50.

The controller 52 or other controller may be configured to provide control signals to the drive circuitry 36 (when included) and/or to the motor 37. In some cases, the controller 52 or other controller may receive a control value based on a motor parameter from the control schedule component 48 and a calculated or determined current value of a motor state from the motor state estimator 50. In one example, the control values received from the control schedule component may be control load outputs and within the predetermined range of load outputs. Based on comparing the control value to the calculated or determined value, the controller 52 or other controller may determine a control signal for maintaining or adjusting an operation of the motor 37. In some cases, when a large delta occurs between the control value and the calculated or determined value or a threshold value is reached, the controller 52 may send a signal to the drive circuitry 36 and/or the motor 37 to actively brake the motor 37 (e.g., reverse a direction of current provided to the motor 37 or torque on the motor 37). In some cases, the motor may be actively braked until it stops rotating. Controllers in addition to or other than the controller 52 that are configured to determine a motor control signal based on a control value of a parameter compared to a measured, determined, or calculated real time value of the parameter may be utilized. Alternatively or in addition, the controller 52 or other controllers may determine control signals for the motor in one or more other suitable manners to maintain the load output of the motor within the predetermined range of load outputs from the motor.

Along with feedback from the first sensor 44, the second sensor 46, and/or other sensors, the control schedule component 48, the motor state estimator 50, and the controller 52 or other system with a functionally similar configuration may facilitate a closed loop control of the motor 37 and the rotational device 20 based on the feedback from the sensors (e.g., the first sensor 44 and the second sensor 46) and a control schedule of the control schedule component 48. This closed loop control of the motor 37 and the rotational device 20 may facilitate maintaining a load output from the motor within the range of predetermined load outputs from the motor, where the range of predetermined load outputs from the motor is configured to allow adequate load output at the rotational device 20 up to a safe limit that facilitates passing an occlusion without injuring the patient.

In some cases, the controller 52 or other controller may be configured to adjust the range of predetermined load outputs from the motor 37 based on an initial estimate or determined load output from the motor upon startup of the motor and/or after initial rotation of the motor 37 (e.g., initial movement of the motor 37 at startup). For example, at a predetermined time after the initial startup or initial rotation of the motor 37 and/or in response to selection of the button 27, the controller 52 or other controller may determine a load output from the motor 37 (e.g., an initial load output or other load output from the motor 37) and set a reference load output from the motor based on the determined initial load output from the motor 37. Then, based on the reference load output from the motor 37, the controller 52 or other controller may adjust (e.g., shift, expand, or decrease) the range of predetermined load outputs from the motor 37 to account for external loads acting on the atherectomy system 10 at and/or between the motor 37 and the rotational device 20. In some cases, shifting an end point of, expanding, and/or shifting an entirety of the range of predetermined load outputs from the motor 37 may include setting or adjusting a maximum load output from the motor 37 based on the reference load output from the motor 37.

Figure 4:
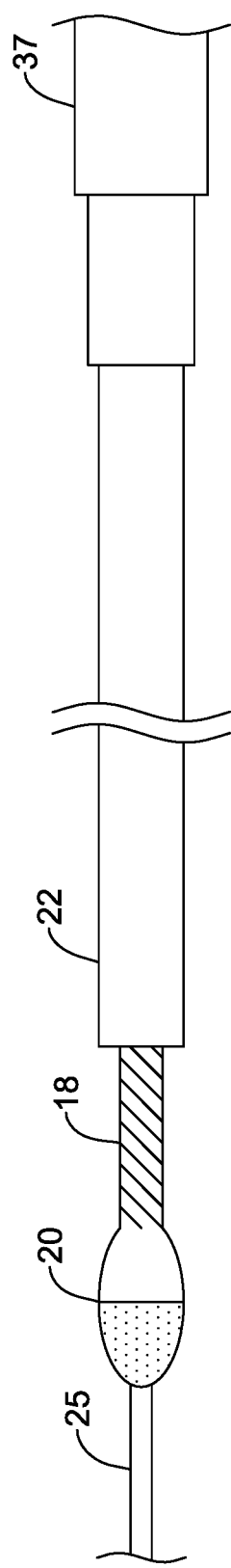
FIG. 4 is a schematic side view of a portion of an example atherectomy system in a straight configuration.
Figure 5:
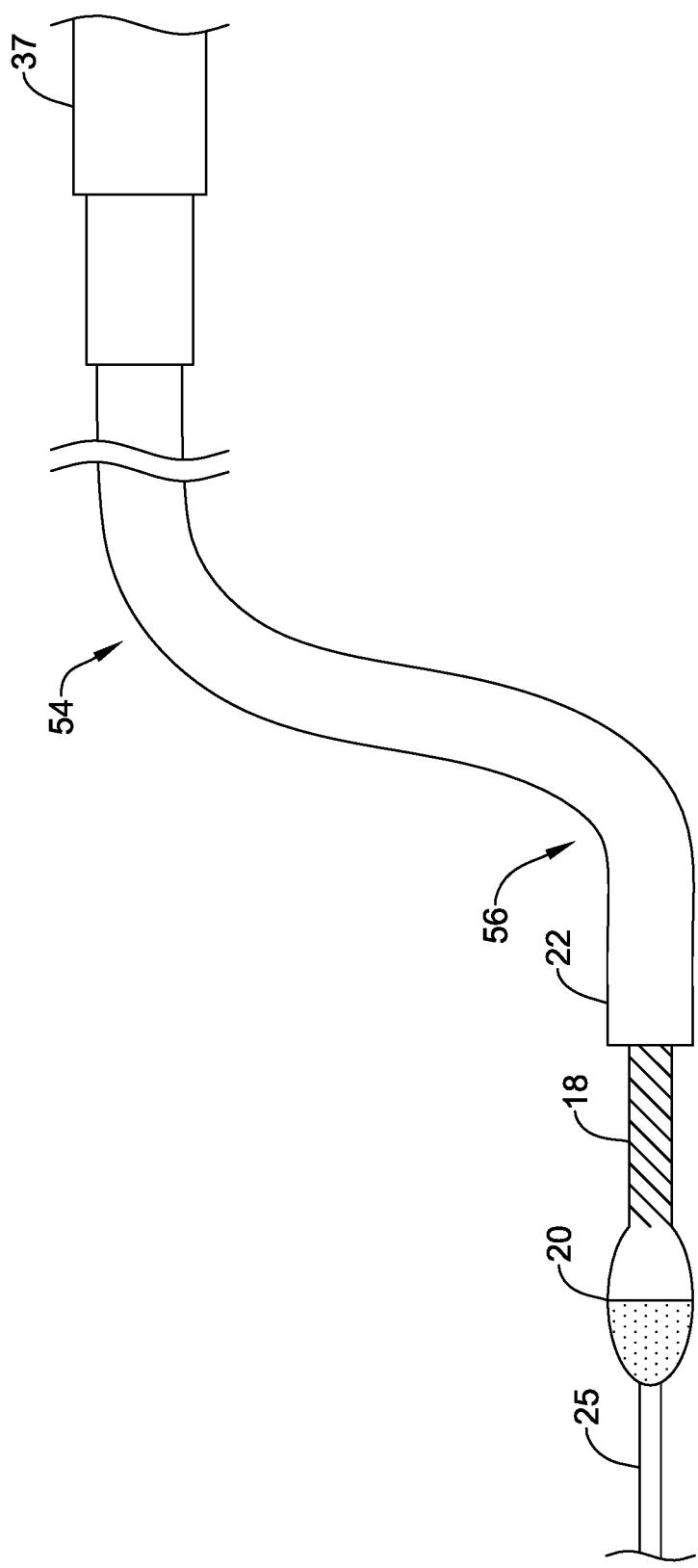
FIG. 5 is a schematic side view of a portion an example atherectomy system in curved configuration.

FIGS. 4 and 5 depict components of the atherectomy system 10 (e.g., the drive shaft 18, the rotational device 20, the elongated member 22, and the motor 37) extending over a guidewire 25, where FIG. 4 depicts the components in a straight configuration and FIG. 5 depicts the components in a bent configuration. The configuration of the components of the atherectomy system 10 depicted in FIG. 5 may be representative of a tortuous path through vessels of a patient, which may occur when the rotational device 20 and/or the drive shaft 18 have been delivered to a position adjacent an occlusion in a patient's vessel.

When the components of the atherectomy system 10 depicted in FIG. 4 are rotated, external loads acting on the components due to bending of the components may be relatively minimal with respect to external loads acting on the components of the atherectomy system 10 depicted in FIG. 5. As such, the predetermined range of load output from the motor 37 may be determined (e.g., determined before use of the atherectomy system 10 in a procedure) when the components of the atherectomy system 10 are in a configuration similar to that shown in FIG. 4. A maximum load output from the motor 37 of the predetermined range of load outputs from the motor 37 may be configured to result in a "safe limit" of torque (e.g., outputted load) at the rotational device 20 for the patient.

As is shown in FIG. 5, the components of the atherectomy system 10 may have one or more bends or curves (e.g., a first bend 54 and a second bend 56, among other bends). Such bends may occur when traversing a tortuous path of a patient's vasculature and/or in other suitable situations. When the components of the atherectomy system 10 depicted in FIG. 5 are rotated, external loads (e.g., drag and/or torque loads) acting on the components due to the bends 54, 56 and/or other bending of the components (e.g., due to the tortuous or otherwise curved path of a patient's vasculature) may be noticeable and may affect a load output from the motor 37 to the rotational device 20. To account for the added external load acting on the components in FIG. 5 when compared to the external load acting on the components in FIG. 4, the reference load output discussed above and in greater detail below may be determined and used to account for the added external load by adjusting the predetermined range of load outputs from the motor 37 to facilitate ensuring adequate load output may be provided to the rotational device 20 for passing an occlusion. Adjusting the predetermined range of load outputs from the motor 37 based on the reference load output may be acceptable without exceeding the "safe limit" of torque (e.g., outputted load) at the rotational device 20 for the patient because the external loads acting on the components of the atherectomy system 10 between the motor 37 and the rotational device 20 may limit an amount of load output supplied at the rotational device 20 to maintain the load output at the rotational device 20 below the "safe limit".

Figure 6:
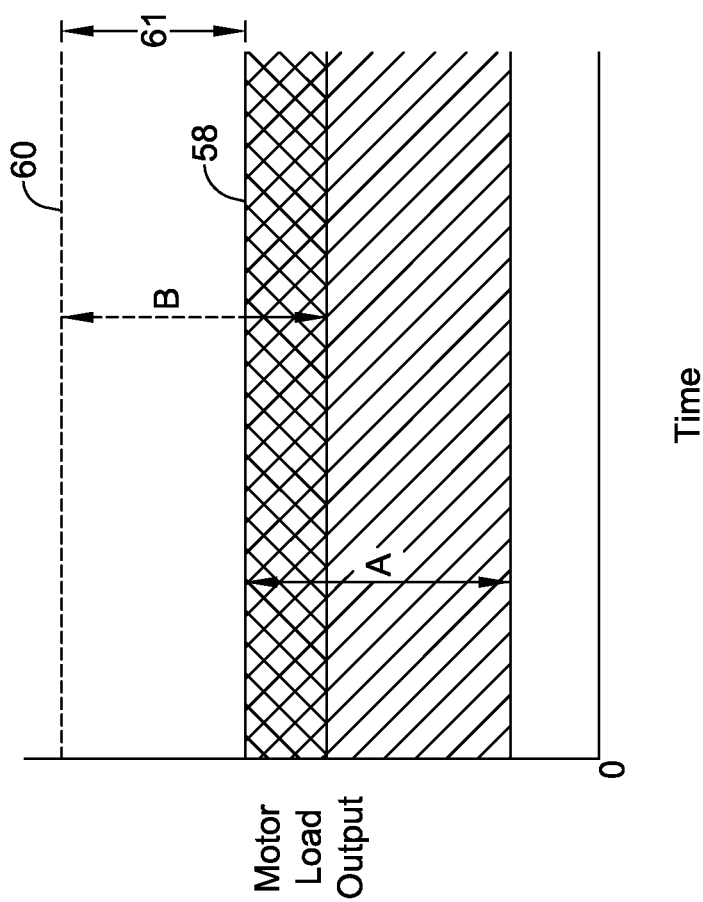
FIG. 6 depicts a graph showing a first range and a second range of load output from a motor without compensation in view of a reference load output from the motor.
Figure 7:
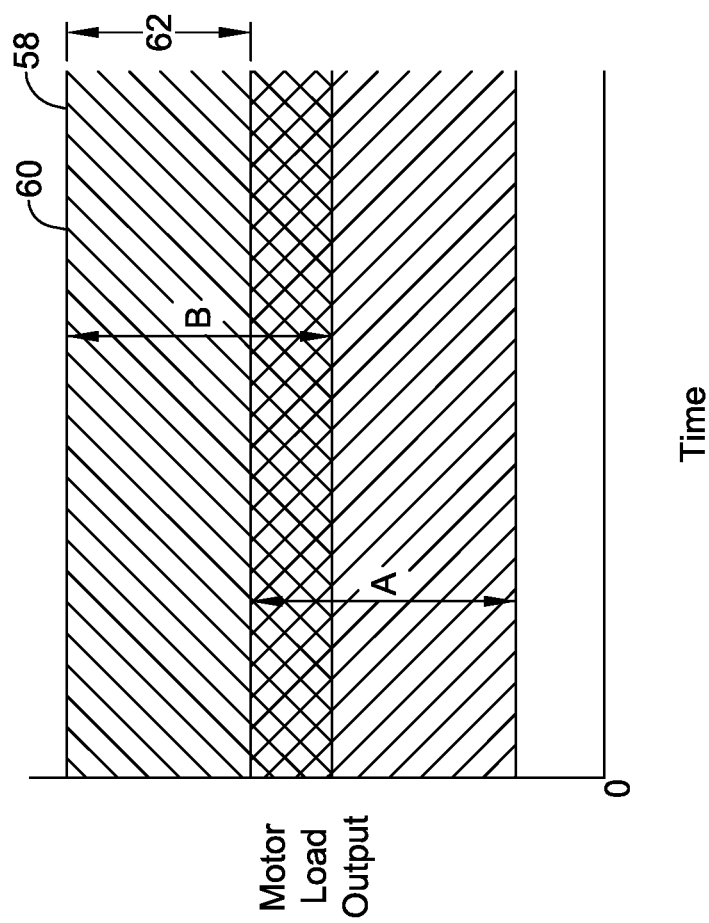
FIG. 7 depicts a graph showing a first range and a second range of load output from a motor with compensation in view of a reference load output from the motor.

FIGS. 6 and 7 depict graphs illustrating ranges of load output from the motor 37 needed when the components of the atherectomy system 10 are in a generally straight configuration without curves or bending (e.g., as shown in FIG. 4) and when the components of the atherectomy system 10 are in a curved or bent configuration (e.g., as shown in FIG. 5). FIGS. 6 and 7 depict a range A of load outputs from the motor 37 that may be safely used to pass through an occlusion when the components of the atherectomy system 10 are configured as shown in FIG. 4, where a lower bound on Range A may be considered a reference load output and an upper bound on Range A may be considered a maximum load output that may result in the "safe limit" of torque at the rotational device 20. Range B depicted in FIGS. 6 and 7 depicts a range of load outputs from the motor 37 that may be required to pass through an occlusion when the components of the atherectomy system 10 are configured as shown in FIG. 5.

Load outputs from the motor 37 may be measured with one or more real time motor parameters. Example real time motor parameters include, but are not limited to, motor speed (e.g., rotations per minute (RPM)), motor torque, drive current, drive voltage, drive power, etc.

Although range A and range B do not extend from zero (0) load output in FIGS. 6 and 7, it is contemplated that range A and/or range B may have a minimum load output of zero (0) (e.g., when a reference load output may be set to zero (0) and/or in other suitable situations). Further, although FIGS. 6 and 7 depict a shift of range A (e.g., a shift or adjustment of both a minimum load output and a maximum load output) to arrive at range B, it is contemplated only one of the minimum load output of range A or the maximum load output of range A may be adjusted to arrive at range B.

FIG. 6 depicts range A and range B, where range A is a fixed predetermined range of possible load outputs from the motor 37 for passing an occlusion (e.g., where Range A may be predetermined while the drive shaft 18 is in the configuration depicted in FIG. 4 and/or other suitable configuration) and range B is a range of load output from the motor needed to pass the occlusion the drive shaft 18 and the rotational device 20 in a suitable manner due to external forces acting thereon when the drive shaft 18 and the rotational device 20 are inserted into a vasculature of a patient. As shown in FIG. 6, if the predetermined range A of load outputs from the motor 37 is a fixed range of load outputs from the motor 37, the control system and the motor 37 of the atherectomy system 10 may not be able to provide adequate load output from the motor 37 to the rotational device 20 for passing through an occlusion in a desired manner due to a maximum amount of load output from the motor 37 (e.g., as represented by line 58) being set to a fixed value below a maximum load output of range B (e.g., a maximum load output from the motor 37 needed to ensure an occlusion is passable in a desired manner, as represented by the line 60 of range B). For example, although range A and range B may overlap, because range A is the fixed possible load outputs from the motor 37 and the maximum of range A is below a maximum of range B (e.g., see difference 61 between line 58 and line 60), a load output at the rotational device 10 may be insufficient for passing an occlusion as a user (e.g., a physician or other user) may not be able use the atherectomy system 10 to pass a target occlusion without stalling out or within a desired amount of time and as a result, causing an increased risk of injury to a patient.

FIG. 7 depicts range A and range B, where a range of possible load outputs from the motor 37 is variable. As shown in FIG. 7, when the range of possible load outputs from the motor 37 is variable, the control system and the motor 37 of the atherectomy system 10 may be able to provide adequate load outputs from the motor 37 to ensure an occlusion is passable in a desired manner when external forces due to bends, curves, and/or factors are acting on the components of the atherectomy system 10 (e.g., as represented by line 58 representing a maximum load output from the motor 37 (and which has been adjusted relative to line 58 in FIG. 6 to meet the needs of range B) and line 60 having the same value). In some cases, a difference 62 between a maximum load output of range A and a maximum load output of range B may be based on the reference load output, as discussed in greater detail below.

Figure 8:
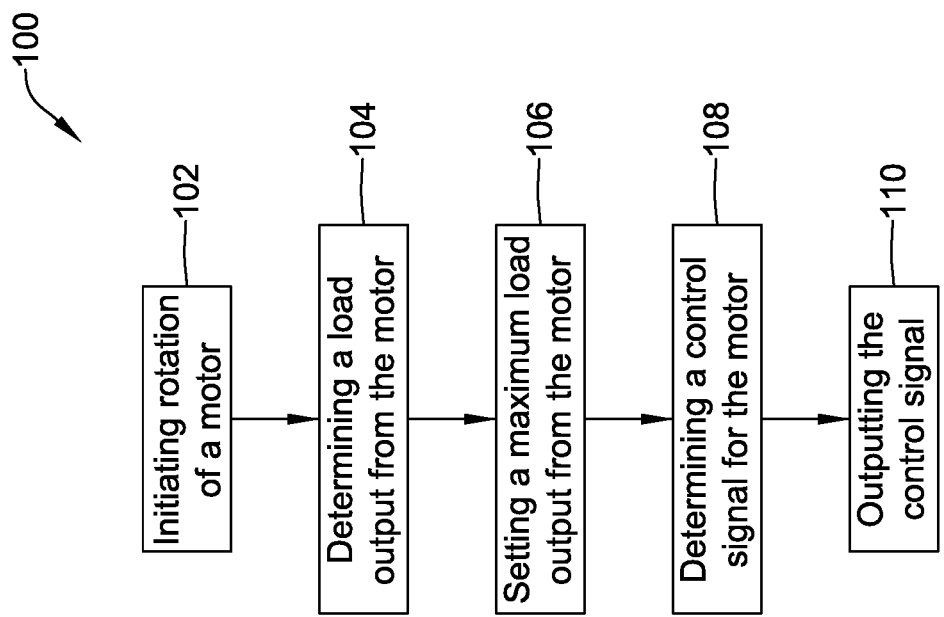
FIG. 8 is a schematic flow diagram of an example method of operating an atherectomy system.

FIG. 8 depicts a method 100 of operating and/or controlling an atherectomy system (e.g., the atherectomy system 10 or other suitable atherectomy system). In some cases, the method 100 of operating and/or controlling the atherectomy system may be incorporated into an atherectomy procedure where a rotational device (e.g., the rotational device 20 or other suitable rotational device) and a drive shaft (e.g., the drive shaft 18 or other suitable drive shaft) of the atherectomy system may be inserted into a vasculature of a patient to a location in a vessel adjacent an occlusion. To account for external loads acting on the atherectomy system due to a tortuous nature of the patient's vasculature, the method 100 may be performed to adjust a load output of a motor (e.g., the motor 37 or other suitable motor) of the atherectomy system to ensure adequate load is provided at the rotational device for crossing the occlusion.

The method 100 may include initiating 102 a rotation of a motor. In some cases, the drive shaft and the rotational device of the atherectomy system may be delivered through vasculature of a patient to a location adjacent an occlusion with the motor in an off mode or without causing rotation of the drive shaft 18 and/or rotational device 20 with the motor. As such, when the rotational device reaches a location adjacent the occlusion, the motor may enter an on mode (e.g., startup in response to user or other control actuation) and the motor may be initially rotated.

Once the motor is started and/or has initially rotated, a load output (e.g., an initial load output) from the motor may be determined 104. In some cases, the load output from the motor may be determined based on feedback from sensors (e.g., sensors 44, 46 and/or other suitable sensors) when the rotational device of the atherectomy system is adjacent the occlusion, but has not yet engaged the occlusion. Such a determined load output from the motor may be set as a reference load output and saved in memory (e.g., the memory 40 or other suitable memory). In some cases, the determined load output from the motor is may be compared to an expected load output and/or a threshold load output from the motor to determine the reference load output, but this is not required.

Once the motor is started up and/or has initially rotated, a value of a maximum load output from the motor may be set 106. In some cases, the control system of the atherectomy system may set the value of the maximum load output of the motor to a value based on the determined load output from the motor. The value of the maximum load output from the motor may be set in one or more of a variety of manners including, but not limited to, shifting the predetermined range of load outputs from the motor, adjusting an upper bound of the predetermined range of load outputs from the motor, adjusting a lower bound of the predetermined range of load outputs from the motor, and/or setting the maximum load output of the motor in one or more other manners. Once set, the value of the maximum load output of the motor may be saved in memory for access by a processor (e.g., the processor 38 or other suitable processor) and/or for other purposes.

In some cases, the maximum load output from the motor may be a function of or may be based on the reference load output of the motor. In such cases, the determined load output from the motor may be the reference output load of the motor or a value of a function that is based on the determined load output of the motor.

When setting the maximum load output from the motor to a value based on the reference load output from the motor by shifting the predetermined range of load outputs, the predetermined range of load outputs may be effectively shifted in a variety of manners. In one example, the predetermined minimum load output, the predetermined maximum load output, and/or the predetermined values between the minimum load output and the maximum load output of the predetermined range of load outputs may be shifted based on a value of the reference load output from the motor. In one case, if the reference load output from the motor is X and the predetermined range of load outputs is a range between Y (e.g., the predetermined minimum load output from the motor) and Z (e.g., the predetermined maximum load output from the motor), an adjusted predetermined range of load outputs in view of the reference load output may be a range between a value of $Y+f(X)$ and $Z+f(X)$. In some cases $f(X)$ may be equal to X, but this is not required. Values Y and Z may be predetermined values, such that each of $Y+f(X)$ and $Z+f(X)$ is a value that is a predetermined value greater than the reference load output from the motor. Alternatively or in addition, only one of the minimum value of the predetermined range of load outputs and the maximum value of the predetermined range of load output may be adjusted.

In another example, when the predetermined range of load outputs from the motor is a function of the reference load output from the motor, a tare function may be performed and the reference load output from the motor may be re-set to zero (0). When the tare function is performed, the control system of the atherectomy system may use a same predetermined range of load outputs from the motor regardless of the reference load output from the motor and instead adjust control signal values and/or other values based on the determined load output from the motor and/or the reference load output from the motor. When using the tare function to set the maximum load output from the motor, the maximum load output from the motor may be a predetermined value greater than zero (0) or other value.

In some cases, a control system (e.g., including the controller 52 or other suitable controller) may be configured to automatically determine the load output from the motor and set a maximum load output from the motor after the motor is started and/or initially rotated. In one example, the control system may automatically determine load output from the motor and set a maximum load output from the motor at a predetermined time after the motor is started and/or initially rotated. Example predetermined times may include, but are not limited to, 0.5 seconds, one (1) second, two (2) seconds, five (5) seconds, ten (10) seconds and/or other suitable times after startup of the motor and/or initial rotation of the motor.

As discussed above, the atherectomy system may include a selectable button (e.g., the button 27 or other suitable button) that may be selected or otherwise actuated to initiate determining the load from the motor and set a maximum load output of the motor after the motor is started and/or initially rotated. In one example, the button, when included, may be actuated to initially set the maximum load output from the motor using one or more of the techniques described herein or other suitable techniques. Additionally or alternatively, the button may be actuated to set the maximum load output from the motor using one or more of the techniques described herein or other suitable techniques at any suitable time during operation of the atherectomy system. In an example, the button may be first actuated to initiate initially setting the maximum load output from the motor and then subsequently actuated again to set the maximum load output from the motor a second time. Such an instance may occur when the rotational device 20 and/or drive shaft 18 has been repositioned in a patient's vasculature during a procedure and/or in one or more other suitable instances. In a further, example, the atherectomy system may be configured to automatically initiate initially setting the maximum load output from the motor upon startup of the motor and/or initial rotation of the motor at a first time and the button may be subsequently actuated to set the maximum load output from the motor a second time. The button, when included in the atherectomy system, may be utilized to set the maximum load output from the motor in one or more suitable additional or alternative manners.

After setting 106 the maximum load output from the motor, the atherectomy system may be configured to determine 108 a control signal for the motor. The control signal may be configured in any suitable manners including, but not limited to, the techniques discussed herein such that the load output from the motor is below a set maximum load output from the motor and yet, sufficient to provide enough load to the rotational device for passing an occlusion in view of external loads (e.g., loads acting on the drive shaft, the rotational device, the elongated member, and/or loads acting on other components of the atherectomy system that affect transfer of the load output from the motor to the rotational device). Once the control signal has been determined 108, a controller of the atherectomy system may output 110 the control signal to the motor or other component of the atherectomy system to control the motor and rotation of the rotational device in accordance with the control signal to ensure load outputs from the motor are adequate for passing an occlusion and remain below the set maximum load output from the motor.

Figure 9:
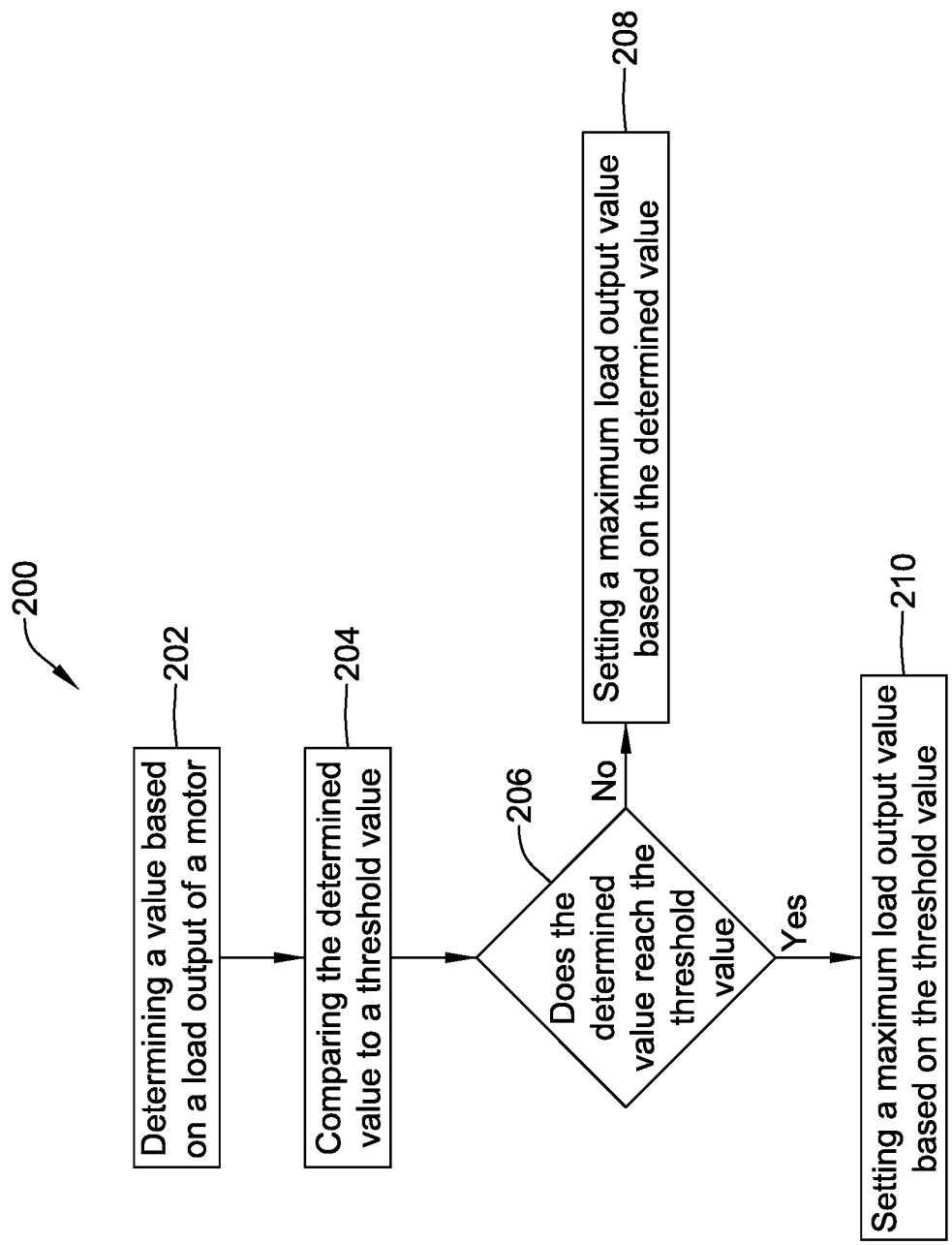
FIG. 9 is a schematic flow diagram of an example method of operating an atherectomy system.

FIG. 9 depicts a method 200 of ensuring a set maximum load output of a motor (e.g., the motor 37 or other suitable motor) of an atherectomy system (e.g., the atherectomy system 10 or other suitable atherectomy system) does not go beyond a safe limit value for load output from the motor. Safe limit values for the load output from the motor may be set based on a variety of factors including, but not limited to, atherectomy procedural techniques and/or configurations of components of the atherectomy system such as the motor, configurations of a drive shaft (e.g., the drive shaft 18 or other suitable drive shaft), configurations of the rotational device (e.g., the rotational device 20 or other suitable rotational device), configurations of a catheter or sheath (e.g., the elongated member 22 or other suitable elongated member), and/or one or more other components of the atherectomy system.

In the method 200, a value based on a load output of the motor may be determined 202. In some cases, the determined 202 value based on the load output of the motor may be considered a load output reference value, but this is not required. The determined value based on the load output of the motor may be equal to a load output from the motor (e.g., a determined or estimated load output from the motor, as discussed herein) and/or may be a function of the load output from the motor. In some cases, the determined value based on the load output from the motor may be stored in memory (e.g., the memory 40 or other suitable memory).

After determining the value based on the load output from the motor, the method 200 may include comparing 204 the determined value to a threshold value. In some cases, the determined value may be the reference load output value and the threshold value may be a threshold reference load output value.

The threshold value may be associated with "safe limit" load output value for the atherectomy system, similar to the "safe limit" values discussed above, but this is not required. In one example use of the threshold value, the threshold value may be utilized and configured to facilitate ensuring a load output at the rotational device does not exceed the safe limit.

When comparing 204 the determined value to the threshold value, a determination 206 may be made by a controller (e.g., the controller 52 or other suitable controller) of the atherectomy system as to whether the determined value reaches or goes beyond the threshold value. Alternatively, a user may make the determination in step 206 and input the result of the comparison to the atherectomy system.

When the determined value has not reached or gone beyond the threshold value, a user or the controller of the atherectomy system may set 208 a value of a maximum load output from the motor based on the determined value. In one example, the value of the maximum load output from the motor may be equal to a sum of a predetermined amount of load output from the motor (e.g., a width of a predetermined range of acceptable load outputs from the motor) and the determined value or otherwise may be equal to a value of a function of the predetermined amount of load output from the motor and the determined value. In some cases, the maximum load output from the motor may be determined based on the predetermined amount of load output from the motor and the determined value in a manner similar to how the maximum load output from the motor is described as being determined with respect to the step 106 of the method 100 and/or in other suitable manners.

When the determined value has reached or gone beyond the threshold value, a user or the controller of the atherectomy system may set 210 a value of a maximum load output from the motor based on the threshold value. In one example, the value of the maximum load output from the motor may be equal to a sum of the predetermined amount of load output from the motor and the threshold value or otherwise may be equal to a value of a function of the predetermined amount of load output from the motor and the threshold value. In some cases, the maximum load output from the motor may be determined based on the predetermined amount of load output from the motor and the threshold value in a manner similar to how the maximum load output from the motor is described as being determined with respect to the step 106 of the method 100 and/or in other suitable manners.

Once determined at step 208 and/or step 210, the value of the maximum load output from the motor may be stored in memory for access by a processor (e.g., the processor 38 or other processor). In some cases, the controller of the atherectomy system may determine and output control signals for the motor in view of the determined maximum load output from the motor in a manner similar to as discussed above with respect to steps 108 and 110 of the method 100 and/or in other suitable manners.

Although not necessarily depicted in the FIGS., the methods described herein (e.g., methods 100, 200, and/or other methods) may include one or more steps other than those steps described herein and/or the described steps may be performed in one or more other orders, as desired unless an expressly indicated otherwise. Moreover, the methods described herein may be repeated during operation of the atherectomy system 10 upon request or initiation, continuously, continuously at predetermined intervals, and/or at other times.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An atherectomy device comprising:
    a drive shaft;
    an atherectomy tip coupled to a first end of the drive shaft;
    a motor coupled to a second end of the drive shaft and configured to rotate the atherectomy tip at an atherectomy procedure rotations per minute (RPM) level; and
    a controller configured to control a load output from the motor, the controller is configured to set a maximum load output from the motor after initial rotation of the motor to achieve rotation of the atherectomy tip at the atherectomy procedure RPM level.

2. The atherectomy device of claim 1, wherein the controller is configured to determine a load output from the motor after initial rotation of the motor and set the maximum load output from the motor based on the determined load output from the motor.

3. The atherectomy device of claim 2, wherein the controller has a predetermined range of allowable load outputs from the motor and the controller is configured to shift the predetermined range of allowable load outputs based on the determined load output from the motor to set the maximum load output from the motor.

4. The atherectomy device of claim 2, wherein the controller is configured to set the maximum load output from the motor to a value that is a predetermined value greater than the determined load output from the motor.

5. The atherectomy device of claim 2 wherein the controller is configured to:
    compare the determined load output from the motor to a threshold value;
    if the determined load output from the motor reaches or goes beyond the threshold value, set a reference load output from the motor to the threshold value;
    if the determined load output from the motor does not reach the threshold value, set the reference load output from the motor to the determined load output from the motor; and
    set the maximum load output from the motor based on the reference load output from the motor.

6. The atherectomy device of claim 1, wherein the controller is configured to set a reference load output from the motor to zero and set the maximum load output from the motor based on the reference load output from the motor.

7. The atherectomy device of claim 6, wherein the controller is configured to set the maximum load output from the motor at a predetermined level greater than zero.

8. The atherectomy device of claim 6, further comprising:
    a button; and
    wherein the controller is configured to set the reference load output from the motor to zero upon actuation of the button.

9. The atherectomy device of claim 6, wherein the controller is configured to automatically set the reference load output from the motor to zero at a predetermined time after initial rotation of the motor.

10. The atherectomy device of claim 1, further comprising:
    a button; and
    wherein the controller is configured to set the maximum load output from the motor upon actuation of the button.

11. The atherectomy device of claim 1, wherein the controller is configured to automatically set the maximum load output from the motor at a predetermined time after initial rotation of the motor.

12. The atherectomy device of claim 1, further comprising:
    a button; and
    wherein the controller is configured to set the maximum load output from the motor at a first time after initial rotation of the motor and set the maximum load output from the motor at a second time after initial rotation of the motor in response to actuation of the button, the second time is after the first time.

13. A method of controlling an atherectomy medical device, the method comprising:
    determining a load output from a motor of an atherectomy medical device after a startup of the motor;
    setting a maximum load output from the motor based on the determined load output from the motor to achieve rotation of an atherectomy tip in communication with the motor at an atherectomy procedure rotations per minute (RPM) level;
    determining a control signal for the motor that is configured to establish a load output from the motor that is less than the set maximum load output from the motor and achieve the atherectomy procedure RPM level of the atherectomy tip; and
    outputting the control signal to maintain the load output from the motor below the set maximum load output from the motor.

14. The method of claim 13, further comprising:
comparing the determined load output from the motor to a threshold reference load output from the motor;
if the determined load output from the motor does not reach or go beyond the threshold reference load output from the motor, setting the maximum load output from the motor to a value based on a predetermined load output amount and the determined load output from the motor; and
if the determined load output from the motor reaches or goes beyond the threshold reference load output from the motor, setting the maximum load output from the motor to a value based on the predetermined load output amount and the threshold reference load output from the motor.

15. The method of claim 13, further comprising:
setting a reference load output from the motor based on the determined load output from the motor; and
wherein the set maximum load output from the motor is based on a predetermined load output amount and the set reference load output from the motor.

16. The method of claim 15, wherein the reference load output from the motor is set to zero when the determined load output from the motor has not reached or gone beyond a threshold reference load output from the motor.

17. A controller for an atherectomy medical device, the controller comprising:
a processor; and
memory in communication with the processor; and
wherein the processor is configured to:
determine a load output from a motor of an atherectomy medical device having an atherectomy tip configured to rotate at an atherectomy procedure rotations per minute (RPM) level in response to the load output from the motor;
set a maximum load output from the motor based on the determined load output from the motor to achieve the atherectomy procedure RPM level at the atherectomy tip and store the set maximum load output in the memory; and
output a control signal to the motor configured to achieve a load output from the motor that is less than the set maximum load output of the motor.

18. The controller of claim 17, wherein the processor is configured to:
compare the determined load output from the motor to a threshold reference load output from the motor;
if the determined load output from the motor does not reach or go beyond the threshold reference load output from the motor, set the maximum load output from the motor to a value based on a predetermined amount of load output and the determined load output from the motor; and
if the determined load output from the motor reaches or goes beyond the threshold reference load output from the motor, set the maximum load output from the motor to a value based on the predetermined amount of load output and the threshold reference load output from the motor.

19. The controller of claim 17, wherein the controller is configured to set the maximum load output from the motor in response to actuation of a tare button.

20. The controller of claim 17, wherein the controller is configured to automatically set the maximum load output from the motor at a predetermined time after initial rotation of the motor.

* * * * *